United States Patent [19]

Stainer

[11] Patent Number: 5,171,350

[45] Date of Patent: Dec. 15, 1992

[54] BIOCIDE

[75] Inventor: Philip J. Stainer, Haverhill, Great Britain

[73] Assignee: Advanced Chemical Products Limited, England

[21] Appl. No.: 673,851

[22] Filed: Mar. 21, 1991

Related U.S. Application Data

[63] Continuation of Ser. No. 180,368, Apr. 11, 1988, abandoned.

[30] Foreign Application Priority Data

Apr. 9, 1987 [GB] United Kingdom ............... 8708501

[51] Int. Cl.$^5$ ............................................. A01N 59/20
[52] U.S. Cl. ...................................... 71/67; 514/642; 514/738
[58] Field of Search ..................... 514/642, 738; 71/67

[56] References Cited

U.S. PATENT DOCUMENTS 4,499,077 2/1985 Stockel et al. ................... 514/642
4,719,083 11/1988 Baker et al. ..................... 514/642

FOREIGN PATENT DOCUMENTS 0059978 9/1982 European Pat. Off. .

Primary Examiner—Frederick E. Waddell
Assistant Examiner—Zohreh A. Fay
Attorney, Agent, or Firm—Ostrolenk, Faber, Gerb & Soffen

[57] ABSTRACT

A biocidal composition for the treatment of water comprises a cationic polyquaternary ammonium biocide, together with a source of transition metal cations e.g. copper II cations and/or a biocide of the type containing a gem. bromonitromethylene group e.g. 2-bromo-2-nitropropane-1,3-diol.

10 Claims, No Drawings

BIOCIDE

This is a continuation of application Ser. No. 07/180.368 filed on Apr. 11, 1988, now abandoned.

This invention relates to biocidal compositions for the treatment of water, and to methods for preventing microbial growth in water.

When water is used or retained in an open environment where it is subject to contamination by microorganisms, maintaining a suitable degree of sterility can be a problem. For example, recirculating water in cooling towers tends to become fouled by algal growths and bacterial slimes. Swimming pools become contaminated with algae and then by potentially dangerous bacteria. Similarly, industrial and agricultural lagoons. Process water from various industrial applications such as paper milling, and other recycled water, need to be treated to control microbiological growths.

Various agents have been proposed, and are commonly used, for the control of algae. The most frequently used today are oxidative substances such as hydrogen peroxide, sodium hypo-chlorite, and quaternary ammonium compounds such as n-alkyl dimethylbenzylammonium chlorides and n-alkyl dimethyl ethylbenzylammonium chlorides and analogous compounds. These substances are used to prevent microbial growth: that is to say they are added to water which has already been cleaned and sterilized (e.g. by filtration and chlorination), in order to maintain sterility. They are effective, typically at levels in the water of 10-100 ppm, although they do not necessarily provide a particularly wide spectrum of antimicrobial activity.

It is also well known that cations of transition metals such as copper and cobalt have algaecidal properties. Copper is particularly noted in this respect but has little, if any, activity against bacteria. One problem with the use of copper salts is that they tend to break down under neutral or slightly basic conditions to yield a precipitate of hydrated copper II hydroxide.

We have now discovered that a combination of transition metal cations, especially copper II cations, with a cationic polyquaternary ammonium biocidal compound or a quaternary ammonium biocide comprising one long chain alkyl group and three other groups selected from lower alkyl and aralkyl groups, has advantageous properties.

In particular, the combination of the quaternary compound and the metal ions in a concentrated aqueous system provides a stabilized metal ion solution which does not precipitate on dilution in the water to be treated. It may be theorized that the combination comprises some form of complex, since characteristic colour changes occur, e.g. the formation of an intense deep blue colour in dilute aqueous solutions of the copper II complex. The result is a distinct stabilization of the metal ions.

Thus, if copper sulphate (the blue pentahydrate) is dissolved in a concentrated aqueous solution of the quaternary ammonium compound, a clear common solution is formed. This solution can be added to the water, typically to give a quaternary compound level of 40 ppm and a copper level of 2.4 ppm without any precipitation of copper hydroxides or salts on dilution.

The quaternary compounds of choice are poly[hydroxyethylene(dimethylimino)β'-hydroxypropyl dimethylimino)methylene-dichloride], hereinafter referred to as PHE, such as the product sold by ABM Chemicals Limited of Woodley. Stockport, Cheshire SK6 1PQ ; poly[2-hydroxyethylene(dimethylimino)ethylene(dimethylimino) methylene dichloride]; and poly[hydroxyethylene(dimerhylimino)ethylene(dimethylimino)ethylene dichloride]. Other polymeric quaternary compounds comprise those carrying quaternised nitrogen atoms on side chains. Polyquaternary compounds are much preferred, giving good solubility and long lasting stability on dilution. Quaternary compounds such as didecyldimethyl ammonium chloride are unsatisfactory and tend to form insoluble complexes. Single quaternary compounds can be used, however, if the nitrogen atom is substituted by only one long chain alkyl group (e.g. $C_{12}$–$C_{18}$), the remaining three substituents being lower alkyl, e.g. methyl, groups or aralkyl groups, e.g. benzyl or ethylbenzyl groups.

Typically, the transition metal ion content in the mixture should be sufficient to give a level of about 0.5 to 3 ppm in the treated water when the quaternary compound is present in the water at about 30 to 50 ppm. The metal is advantageously copper, but may for example be zinc, chromium or tin.

The concentrated mixture for addition to water can contain up to 50 or 60% of the quaternary compound and an equivalent amount of copper or other transition metal ions.

We provide, therefore, a biocidal composition containing a polymeric quaternary biocide, together with transition metal cations, especially copper II cations, and also a method of controlling microorganisms in water using such a composition.

In a separate feature of the invention, we have found that the quaternary biocides can also be enhanced in their bactericidal activity by formulation with a biocide of the type comprising a carbon atom substituted by a halogen atom and a nitro group, e.g. cyclic

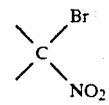

compounds and also 2-bromo-2-nitropropane-1,3-diol, supplied under the brand names Myacide by Boots Pure Drug Co., Nottingham and Bronopol by Henkel & Cie and 5-bromo-5-nitro-1,3-dioxane supplied under the brand name Bronidox by Henkel & Cie. These biocides have activity against a wider range of bacteria than quaternaries, and especially are active against pseudomonads. Myacide is usually used at a level of about 50-100 ppm.

Surprisingly we have now found that if Myacide or the like is formulated with a quaternary such as Glokill PQ so that at a dilution in water of the quaternary of about 20-30 ppm, the Myacide etc is present at about 0.5 to 5 ppm, the formulation is active against pseudomonads as well, even though the Myacide is present at levels far below those normally considered necessary. The two substances are mutually compatible, forming a stable co-solution concentrate and provide a powerful biocidal action on all water environments, especially pools and cooling towers. We therefore provide as a further feature of the invention biocidal compositions containing a halonitro biocide, and a quaternary biocide a ratio of from 1:50 to 1:10 by weight, and also a method of controlling microorganisms in water, using such a composition.

EXAMPLE 1

Microbiological Activity (1)

Three samples were compared:
Sample 1:

|  | % by weight |
|---|---|
| PHE | 83.0 |
| 2-bromo-2-nitro-propan-1,3-diol (BNP) | 2.5 |
| $CuSO_4$ | 7.0 |
| 4N HCl | 0.5 |
| Mains water | 7.0 |

Sample 2: As Sample 1, but omitting the BNP
Sample 3: As Sample 1, but omitting the copper salt
Sample 4 As Sample 1, but replacing the BNP by 5-bromo-5-nitro-1,3-dioxan.

Methods

1. Culture Preparation

A 24 hour Tryptone Soya Agar (TSA) sloped culture of *Pseudomonas aeruginosa* NCTC 6750 was washed off using sterile distilled water (SDW) and diluted in SDW to approx. $10^8$ organisms per ml.

2. Kill Tests

A range of dilutions of the test solutions were prepared in sterile standard World Health Organisation (WHO) Hard Water (see Appendix 1). At zero time *P. aeruginosa* inoculum was added to each dilution of each test solution to give approx. $10^6$ organisms per ml. A control of sterile standard WHO hard water was also included. The tests were stored at 22° C. and sampled at 0 hours (control only), 24 hours, 48 hours and 72 hours. The number of viable bacteria was estimated using a pour plate technique (0.1% peptone water as diluent and TSA as growth medium). The pour plates were incubated at 30° C. for 3 days, surviving colonies counted and the dilution giving a 99.99% reduction in the bacterial population for each contact time calculated. The test was carried out on two separate occasions.

Results

The number of surviving organisms for each test sample at each dilution and sampling time are shown in Tables 1 to 8

TEST 1—PRELIMINARY RANGE FINDING TEST

TABLE 1

Sample 1
Number of organisms per ml surviving in

| Dilution | ppm Product | 0 | 24 | 48 | 72 |
|---|---|---|---|---|---|
| Control | 0 | $4.5 \times 10^6$ | $5.9 \times 10^6$ | $3.0 \times 10^6$ | $1.9 \times 10^6$ |
| 1:5,000,000 | 0.2 | — | $4.6 \times 10^6$ | $5.6 \times 10^6$ | $5.7 \times 10^6$ |
| 1:2,000,000 | 0.5 | — | $4.7 \times 10^6$ | $6.9 \times 10^6$ | $9.8 \times 10^6$ |
| 1:1,000,000 | 1.0 | — | $6.8 \times 10^3$ | $2.6 \times 10^6$ | $1.8 \times 10^6$ |
| 1:500,000 | 2.0 | — | $3.4 \times 10^3$ | $7.9 \times 10^3$ | $1.9 \times 10^5$ |
| 1:200,000 | 5.0 | — | $2.2 \times 10^3$ | $3.9 \times 10^4$ | $1.2 \times 10^5$ |
| 1:100,000 | 10.0 | — | $2.0 \times 10^1$ | <10 | $1.4 \times 10^2$ |

— count not required.

TABLE 2

Sample 2
Number of organisms per ml surviving in

| Dilution | ppm Product | 0 | 24 | 48 | 72 |
|---|---|---|---|---|---|
| Control | 0 | $4.5 \times 10^6$ | $5.9 \times 10^6$ | $3.0 \times 10^6$ | $1.9 \times 10^6$ |
| 1:5,000,000 | 0.2 | — | $3.7 \times 10^6$ | $6.8 \times 10^6$ | $8.5 \times 10^6$ |
| 1:2,000,000 | 0.5 | — | $3.7 \times 10^6$ | $5.2 \times 10^6$ | $5.9 \times 10^6$ |
| 1:1,000,000 | 1.0 | — | $3.0 \times 10^4$ | $7.6 \times 10^6$ | $5.1 \times 10^6$ |
| 1:500,000 | 2.0 | — | $2.2 \times 10^2$ | $3.2 \times 10^2$ | $8.2 \times 10^4$ |
| 1:200,000 | 5.0 | — | $2.0 \times 10^2$ | $4.1 \times 10^4$ | $1.6 \times 10^5$ |
| 1:100,000 | 10.0 | — | $1.0 \times 10^1$ | <10 | <10 |

— count not required.

TABLE 3

Sample 3
Number of organisms per ml surviving in

| Dilution | ppm Product | 0 | 24 | 48 | 72 |
|---|---|---|---|---|---|
| Control | 0 | $4.5 \times 10^6$ | $5.9 \times 10^6$ | $3.0 \times 10^6$ | $1.9 \times 10^6$ |
| 1:5,000,000 | 0.2 | — | $3.4 \times 10^6$ | $3.9 \times 10^6$ | $5.3 \times 10^6$ |
| 1:2,000,000 | 0.5 | — | $2.9 \times 10^6$ | $3.7 \times 10^6$ | $5.6 \times 10^6$ |
| 1:1,000,000 | 1.0 | — | $4.4 \times 10^5$ | $4.7 \times 10^6$ | $5.8 \times 10^6$ |
| 1:500,000 | 2.0 | — | $7.3 \times 10^4$ | $2.2 \times 10^4$ | $4.0 \times 10^4$ |
| 1:200,000 | 5.0 | — | $3.9 \times 10^2$ | $1.9 \times 10^2$ | $4.3 \times 10^3$ |
| 1:100,000 | 10.0 | — | $1.0 \times 10^1$ | <10 | $1.3 \times 10^2$ |

— count not required.

TABLE 4

Sample 4
Number of organisms per ml surviving in

| Dilution | ppm Product | 0 | 24 | 48 | 72 |
|---|---|---|---|---|---|
| Control | 0 | $4.5 \times 10^6$ | $5.9 \times 10^6$ | $3.0 \times 10^6$ | $1.9 \times 10^6$ |
| 1:5,000,000 | 0.2 | — | $4.3 \times 10^6$ | $5.9 \times 10^6$ | $6.0 \times 10^6$ |
| 1:2,000,000 | 0.5 | — | $1.8 \times 10^6$ | $4.7 \times 10^6$ | $4.3 \times 10^6$ |
| 1:1,000,000 | 1.0 | — | $4.3 \times 10^4$ | $5.2 \times 10^6$ | $9.6 \times 10^6$ |
| 1:500,000 | 2.0 | — | $8.0 \times 10^4$ | $9.3 \times 10^4$ | $5.9 \times 10^5$ |
| 1:200,000 | 5.0 | — | $3.5 \times 10^3$ | $2.5 \times 10^5$ | $3.4 \times 10^4$ |
| 1:100,000 | 10.0 | — | $3.0 \times 10^1$ | $9.6 \times 10^2$ | $5.3 \times 10^4$ |

— count not required.

TABLE 5

TEST 2
Sample 1
Number of organisms per ml surviving in

| Dilution | ppm Product | 0 | 24 | 48 | 72 |
|---|---|---|---|---|---|
| Control | 0 | $2.8 \times 10^6$ | $1.0 \times 10^6$ | $1.4 \times 10^6$ | $1.1 \times 10^7$ |
| 1:1,000,000 | 1.0 | — | $2.8 \times 10^5$ | $8.4 \times 10^6$ | $1.4 \times 10^7$ |
| 1:500,000 | 2.0 | — | $3.9 \times 10^3$ | $5.6 \times 10^3$ | $2.4 \times 10^5$ |
| 1:200,000 | 5.0 | — | $1.2 \times 10^3$ | $8.0 \times 10^2$ | $1.6 \times 10^3$ |
| 1:100,000 | 10.0 | — | $2.7 \times 10^3$ | $3.8 \times 10^2$ | $1.7 \times 10^2$ |
| 1:50,000 | 20.0 | — | $3.0 \times 10^1$ | $1.0 \times 10^1$ | <10 |
| 1:20,000 | 50.0 | — | $9.0 \times 10^2$ | <10 | <10 |
| 1:10,000 | 100.0 | — | $5.0 \times 10^2$ | $2.0 \times 10^1$ | <10 |

— count not required.

TABLE 6

Sample 2
Number of organisms per ml surviving in

| Dilution | ppm Product | 0 | 24 | 48 | 72 |
|---|---|---|---|---|---|
| Control | 0 | $2.8 \times 10^6$ | $1.0 \times 10^6$ | $1.4 \times 10^6$ | $1.1 \times 10^7$ |
| 1:1,000,000 | 1.0 | — | $1.9 \times 10^6$ | $1.4 \times 10^7$ | $8.4 \times 10^6$ |
| 1:500,000 | 2.0 | — | $2.7 \times 10^3$ | $9.0 \times 10^3$ | $3.4 \times 10^5$ |
| 1:200,000 | 5.0 | — | $1.4 \times 10^3$ | $3.7 \times 10^3$ | $2.8 \times 10^5$ |
| 1:100,000 | 10.0 | — | $1.3 \times 10^3$ | $1.8 \times 10^3$ | $1.5 \times 10^4$ |
| 1:50,000 | 20.0 | — | <10 | $1.0 \times 10^1$ | $1.0 \times 10^2$ |
| 1:20,000 | 50.0 | — | $2.5 \times 10^3$ | <10 | $1.6 \times 10^2$ |

TABLE 6-continued

Sample 2
Number of organisms per ml surviving in

| Dilution | ppm Product | Time in hours | | | |
|---|---|---|---|---|---|
| | | 0 | 24 | 48 | 72 |
| 1:10,000 | 100.0 | — | $1.0 \times 10^1$ | <10 | <10 |

— count not required.

TABLE 7

Sample 3
Number of organisms per ml surviving in

| Dilution | ppm Product | Time in hours | | | |
|---|---|---|---|---|---|
| | | 0 | 24 | 48 | 72 |
| Control | 0 | $2.8 \times 10^6$ | $1.0 \times 10^6$ | $1.4 \times 10^6$ | $1.1 \times 10^7$ |
| 1:1,000,000 | 1.0 | — | $2.6 \times 10^6$ | $9.2 \times 10^6$ | $8.4 \times 10^6$ |
| 1:500,000 | 2.0 | — | $6.0 \times 10^4$ | $3.0 \times 10^5$ | $2.3 \times 10^5$ |
| 1:200,000 | 5.0 | — | $1.3 \times 10^3$ | $2.4 \times 10^3$ | $1.5 \times 10^4$ |
| 1:100,000 | 10.0 | — | $1.8 \times 10^3$ | $6.0 \times 10^2$ | $1.5 \times 10^3$ |
| 1:50,000 | 20.0 | — | $1.2 \times 10^3$ | $2.0 \times 10^1$ | <10 |
| 1:20,000 | 50.0 | — | $6.0 \times 10^2$ | $3.0 \times 10^1$ | <10 |
| 1:10,000 | 100.0 | — | $3.0 \times 10^1$ | <10 | <10 |

— count not required.

TABLE 8

Sample 4
Number of organisms per ml surviving in

| Dilution | ppm Product | Time in hours | | | |
|---|---|---|---|---|---|
| | | 0 | 24 | 48 | 72 |
| Control | 0 | $2.8 \times 10^6$ | $1.0 \times 10^6$ | $1.4 \times 10^6$ | $1.1 \times 10^7$ |
| 1:1,000,000 | 1.0 | — | $3.4 \times 10^6$ | $1.4 \times 10^7$ | $8.0 \times 10^6$ |
| 1:500,000 | 2.0 | — | $1.9 \times 10^3$ | $4.0 \times 10^3$ | $6.0 \times 10^5$ |
| 1:200,000 | 5.0 | — | $2.0 \times 10^1$ | $9.0 \times 10^1$ | $9.0 \times 10^2$ |
| 1:100,000 | 10.0 | — | $1.0 \times 10^1$ | $2.0 \times 10^1$ | $2.3 \times 10^4$ |
| 1:50,000 | 20.0 | — | <10 | <10 | <10 |
| 1:20,000 | 50.0 | — | <10 | <10 | <10 |
| 1:10,000 | 100.0 | — | <10 | <10 | <10 |

— count not required.

CALCULATIONS

Linear regression was used to plot graphs of the log of number of colony forming units per ml. versus ppm of product. From these graphs the concentration of each product required, at each sampling time, to give 99.99% reduction in the bacterial population was determined. The values thus obtained for Test 1 and Test 2, and the corresponding dilution factors, are depicted in Tables 9 and 10.

TABLE 9

TEST 1

| Product | Contact time in hours | Product required to give 99.99% reduction in bacterial numbers | |
|---|---|---|---|
| | | ppm | dilution |
| Sample 1 | 24 | 6.3 | 1:158,730 |
| | 48 | 7.6 | 1:132,450 |
| | 72 | 10.1 | 1:99,009 |
| Sample 2 | 24 | 5.5 | 1:183,486 |
| | 48 | 6.6 | 1:151,515 |
| | 72 | 7.4 | 1:134,589 |
| Sample 3 | 24 | 6.3 | 1:159,235 |
| | 48 | approx 12.0 | 1:83,333 |
| | 72 | approx 15.5 | 1:64,516 |
| Sample 4 | 24 | 6.1 | 1:163,934 |
| | 48 | 5.9 | 1:169,491 |
| | 72 | 9.0 | 1:111,111 |

TABLE 10

TEST 2

| Product | Contact time in hours | Product required to give 99.99% reduction in bacterial numbers | |
|---|---|---|---|
| | | ppm | dilution |
| Sample 1 | 24 | 105.2 | 1:9,505 |
| | 48 | 44.5 | 1:22,471 |
| | 72 | 24.0 | 1:41,666 |
| Sample 2 | 24 | 60.5 | 1:16,528 |
| | 48 | 40.5 | 1:24,691 |
| | 72 | 37.5 | 1:26,666 |
| Sample 3 | 24 | 74.5 | 1:13,422 |
| | 48 | 46.0 | 1:21,739 |
| | 72 | 28.0 | 1:35,714 |
| Sample 4 | 24 | 28.5 | 1:35,087 |
| | 48 | 31.5 | 1:31,746 |
| | 72 | 28.5 | 1:35,087 |

APPENDIX

Sterile Standard World Health Organisation Hard Water

Solution a
9.88 g $MgCl_2 \cdot 6H_2O$ in 100 ml distilled water.
Filter sterilise.

Solution b
21.6 g $CaCl_2$(anhydrous) in 100 ml distilled water.
Filter sterilise.

Add 3 ml of solution a, plus 3 ml of solution b to 2 liters of sterile distilled water.

EXAMPLE 2

| Zinc Replacing Copper II | |
|---|---|
| Component | % w/w |
| PHE | 83 |
| BNP | 2.5 |
| $Zn\ SO_4 \cdot 7H_2O$ | 7.0 |
| 4N HCl | 0.5 |
| Mains water | 7.0 |

EXAMPLE 3

Stannic (Tin IV) Replacing Copper II

| | |
|---|---|
| PHE | 83% w/w |
| BNP | 2.5% w/w |
| $SnCl_4$(ANHYD) | 7.0% w/w |
| 4N HCl | 0.5% w/w |
| Mains water | 7.0% 2/w |

EXAMPLE 4

Stannous (Tin II) Replacing Cu II

| When made | |
|---|---|
| PHE | 83% w/w |
| BNP | 2.5% w/w |
| $Sn_2Cl_2 \cdot 2H_2O$ | 7.0% w/w |
| 4N.HCl | 0.5% w/w |
| Tap water | 7.0% w.w |

This product was cloudy when made, but on HEATING turned yellow and began to clear. There may have been some evaporation of the water.

EXAMPLE 5

Buckman WSCP Replacing PHE

| Component | Parts | Final % |
|---|---|---|
| *WSCP | 664 | 83 |
| Myacide | 20 | 2.5 |
| $CuSO_4 5H_2O$ | 56 | 7.0 |
| **4NHCl | 12 | 1.5 |
| ***Water | 48 | 6.0 |

*WSCP claimed to be 60% solids (from Buckman, UK)
**Extra HCl added to lower pH to blue crystal 5.5
***Reduced $H_2O$ to compensate for increased HCl
Note: Product does not go deep blue on dilution. EDTA/DTPA needed to give colouration - which is then deeper than with PHE.

EXAMPLE 6

Further Microbiological Activity Data

1. Algistatic Trials

Minimum inhibitory concentrations (m.i.c.) were obtained against *Chlorella emersonii*.

| Sample | m.i.c. (ppm) |
|---|---|
| Sample 1 | 10 |
| Sample 3 | 10 |
| Sample 2 | 10 |
| Product of Example 2 | 15 |

2. Bactericidal Trials

| a) Test Conditions | |
|---|---|
| Biocide dilutions: | prepared in hard water (342 ppm hardness) |
| Test organism: | *Pseudomonas aeruginosa* NCTC 6750 |
| Temperature: | 22° C. |
| Contact times: | 24, 48 & 72 hours |
| Inactivator: | 3% Tween 80 + 2% Soya Lecithin |
| Result: | concentration giving a mean kill of 99.99%. | b) Results

| | Bactericidal Figure (ppm) | | |
|---|---|---|---|
| Sample | 24 hrs | 48 hrs | 72 hrs |
| Sample 1 | 30 | 20 | 20 |
| Sample 3 | 30 | 20 | 20 |
| Sample 2 | 30 | 20 | 20 |
| Product of Example 6 | 30 | 20 | 20 |

The following conclusions may be drawn.
1. Laboratory test suggest that the PHE/BNP/Cu blend will effectively control algal growth.
2. The PHE/BNP/Cu blend is a very effective bactericidal agent.
3. WSCP and PHE are readily interchangeable so far as the bactericidal performance is concerned.

EXAMPLE 7

Microbiological Activity (2)

(A) Three formulations were studied:

| | Formulation | | |
|---|---|---|---|
| Raw Material | A | B | C |
| PHE | 50 | 50 | 50 |
| BNP | 1 | 2 | 3 |
| Citric Acid Monohydrate | 0.5 | 0.5 | 0.5 |

-continued

| | Formulation | | |
|---|---|---|---|
| Raw Material | A | B | C |
| Water | 100 | 100 | 100 |

All formulations were tested for bactericidal activity in the presence of hard water (200 ppm hardness) with a 4 day contact time. Bacteria isolated from a very heavily contaminated swimming pool, which was proving extremely difficult to control, were used as the inoculum. The formulations were tested at concentrations of 100 and 150 ppm. It provided desirable to add the citric acid in order to ensure stability. Two trials were carried out.

(B) Eight different formulations and a control were used:

| Formulation[a] | 50% PHE | Sample 2 from Ex. 1 | BNP |
|---|---|---|---|
| (1) (Control) | 0 | 0 | 0 |
| (2) | 50 | 0 | 0 |
| (3) | 50 | 50 | 0 |
| (4) | 100 | 50 | 0 |
| (5) | 0 | 0 | 2.5 |
| (6) | 0 | 0 | 5 |
| (7) | 50 | 0 | 2.5 |
| (8) | 50 | 50 | 2.5 |
| (9) | 100 | 50 | 5 |

[a]All values given in ppm.

Each formulation was made up in standard tap water (STW) and 20 ml. amounts of each were challenged with about $10^6$/ml *P. aeruginosa* NCTC 6750. Total viable counts (TVC's) were carried out in B.P. diluent and plated onto TSA at 0, 1, 2, 4 and 24 hours. Tests were stored at room temperature.

RESULTS (A)

| Formulation | Concn. (ppm) | Trial 1 | Trial 2 |
|---|---|---|---|
| A | 150 | +++ | +++ |
| | 100 | ++++ | ++++ |
| B | 150 | + | + |
| | 100 | + | ++ |
| C | 150 | + | − |
| | 100 | + | + |

Key:
−: no growth of bacteria
+: slight growth
++: moderate growth
+++: heavy growth
++++: very heavy growth (B)

Bacterial Count (numbers/ml) in Treated Water Samples

| Formu- | Time (hours) | | | | |
|---|---|---|---|---|---|
| lation | 0 | 1 | 2 | 4 | 24 |
| (1) | $2.8 \times 10^6$ | $2.6 \times 10^6$ | $2.1 \times 10^6$ | $2.8 \times 10^6$ | $4.9 \times 10^5$ |
| (2) | — | $8.0 \times 10^1$ | <10 | <10 | <10 |
| (3) | — | $1.1 \times 10^3$ | $1.0 \times 10^2$ | <10 | <10 |
| (4) | — | $1.4 \times 10^3$ | $6.0 \times 10^1$ | <10 | <10 |
| (5) | — | $2.2 \times 10^6$ | $1.4 \times 10^6$ | $1.2 \times 10^6$ | $2.9 \times 10^5$ |
| (6) | — | $2.2 \times 10^6$ | $1.2 \times 10^6$ | $1.4 \times 10^6$ | $3.3 \times 10^5$ |
| (7) | — | $9.0 \times 10^1$ | <10 | <10 | <10 |
| (8) | — | $2.3 \times 10^1$ | $1.0 \times 10^1$ | <10 | <10 |
| (9) | — | $5.4 \times 10^2$ | $1.0 \times 10^1$ | <10 | <10 |

I claim:

1. A biocide composition effective against *Pseudomonas aeruginosa* in water comprising (a) a biocidally effective amount of a first biocide which is a quaternary ammonium biocide selected from the group consisting of poly[hydroxyethylene(dimethylimino)a'-hydroxypropyl(dimethylimino)methylene dichloride], poly[hydroxyethylene(dimethylimino)ethylene(dimethylimino)methylene dichloride] and poly[hydroxyethylene(dimethylimino)ethylene(dimethylimino)ethylene dichloride];

(b) a biocidally enhancing amount of a second biocide which is 2-bromo-2-nitropropane-1,3-diol; and (c) an algicidally effective amount of a cation of copper, wherein the weight ratio of the first biocide to the second biocide is 4:1 to 17:1.

2. The composition of claim 1, wherein the metal is copper.

3. A method of controlling *Psudomonas aeruginosa* microorganisms in water which comprises the application to the water of a biocide composition according to claim 1 in an amount such that the copper is present in the water in an amount of about 0.5 to 3 ppm.

4. A biocidal composition for the treatment of water comprising 10 parts of poly, an algicidally effective amount of copper sulfate, and one part of 2-bromo-2-nitropropane-1,3-diol.

5. A method of controlling *Psudomonas aeruginosa* microorganisms in water which comprises the application to the water of a biocide composition according to claim 4 in an amount such that the copper is present in the water in an amount of about 0.5 to 3 ppm.

6. The composition of claim 1, wherein the cationic polyquaternary ammonium biocide is poly[hydroxyethylene(dimethylimino)a'-hydroxypropyl(dimethylimino)methylene-dichloride].

7. The composition of claim 6, containing the copper in the form of copper sulfate.

8. A method of controlling *Psudomonas aeruginosa* microorganisms in water which comprises the application to the water of a biocide composition according to claim 6 in an amount such that the copper is present in the water in an amount of about 0.5 to 3 ppm.

9. A method of controlling *Psudomonas aeruginosa* microorganisms in water which comprises the application to the water of a biocide composition according to claim 7 in an amount such that the copper is present in the water in an amount of about 0.5 to 3 ppm.

10. The composition of claim 7 which contains about 0.5 to 3 parts of copper for about 30 to 50 parts of the first biocide.

* * * * *